US010143767B2

(12) United States Patent
Franks et al.

(10) Patent No.: US 10,143,767 B2
(45) Date of Patent: Dec. 4, 2018

(54) AIR PURIFIER WITH FILTER AND SCENT-RELEASING MECHANISM

(71) Applicant: Helen of Troy Limited, St. Michael (BB)

(72) Inventors: John Franks, Hopkinton, MA (US); Rich Thrush, Jersey City, NJ (US)

(73) Assignee: Helen of Troy Limited, St. Michael (BB)

(*) Notice: Subject to any disclaimer, the term of this patent is extended or adjusted under 35 U.S.C. 154(b) by 0 days.

(21) Appl. No.: 14/302,658

(22) Filed: Jun. 12, 2014

(65) Prior Publication Data

US 2014/0369896 A1 Dec. 18, 2014

Related U.S. Application Data

(60) Provisional application No. 61/834,291, filed on Jun. 12, 2013.

(51) Int. Cl.
*A61L 9/12* (2006.01)
*A61L 9/16* (2006.01)

(52) U.S. Cl.
CPC ................ *A61L 9/122* (2013.01); *A61L 9/16* (2013.01); *A61L 2209/11* (2013.01); *A61L 2209/133* (2013.01); *A61L 2209/14* (2013.01)

(58) Field of Classification Search
CPC ............... A61L 9/122; A61L 9/12; A61L 9/16
See application file for complete search history.

(56) References Cited

U.S. PATENT DOCUMENTS 3,419,217 A * 12/1968 White ....................... F24F 3/16 239/58
5,549,720 A * 8/1996 Miller .................... B01D 46/12 55/324
6,319,307 B1 11/2001 Shanks
6,357,726 B1 * 3/2002 Watkins .................. A61L 9/122 261/26

(Continued)

FOREIGN PATENT DOCUMENTS

EP 1827514 9/2007
WO 2013011435 1/2013

OTHER PUBLICATIONS

International Search Report and Written Opinion of the International Searching Authority for PCT/US2014/42048 dated Sep. 24, 2014.

(Continued)

*Primary Examiner* — Regina M Yoo
(74) *Attorney, Agent, or Firm* — Rankin, Hill & Clark LLP

(57) ABSTRACT

An appliance for delivering agent. The agent-delivery appliance includes an agent-releasing mechanism, an air-moving device that generates a flow of air moving from upstream to downstream, and at least one filter. The agent-releasing mechanism includes a chamber configured to release agent into the flow of air generated by the air-moving device. The chamber includes multiple openings, one of which is configured to provide air loaded with agent from the chamber to a first location within the flow of air generated by the air-moving device. At least one filter is located upstream from the first location within the flow of air generated by the air-moving device.

22 Claims, 6 Drawing Sheets

(56) References Cited

U.S. PATENT DOCUMENTS

| | | | |
|---|---|---|---|
| 6,536,746 B2* | 3/2003 | Watkins | A61L 9/122 261/26 |
| 6,770,247 B1* | 8/2004 | Romack | A61L 9/03 261/115 |
| 6,913,733 B2* | 7/2005 | Hardy | A61L 9/014 422/124 |
| 7,776,276 B1 | 8/2010 | Newbolt | |
| 8,071,081 B2* | 12/2011 | Weiss | A61L 9/015 424/405 |
| 2002/0036358 A1* | 3/2002 | Watkins | A61L 9/122 261/26 |
| 2003/0173685 A1* | 9/2003 | Watkins | A61L 9/122 261/26 |
| 2004/0031248 A1 | 2/2004 | Lindsay | |
| 2004/0047776 A1* | 3/2004 | Thomsen | A61L 2/10 422/186.07 |
| 2010/0071554 A1 | 3/2010 | Pfeffer et al. | |
| 2010/0143205 A1 | 6/2010 | Engelhard | |
| 2011/0155150 A1 | 6/2011 | Al-Qassem | |
| 2012/0205460 A1 | 8/2012 | Franks | |

OTHER PUBLICATIONS

Supplementary European Search Report filed in EP 14810522 dated Jan. 23, 2017.

* cited by examiner

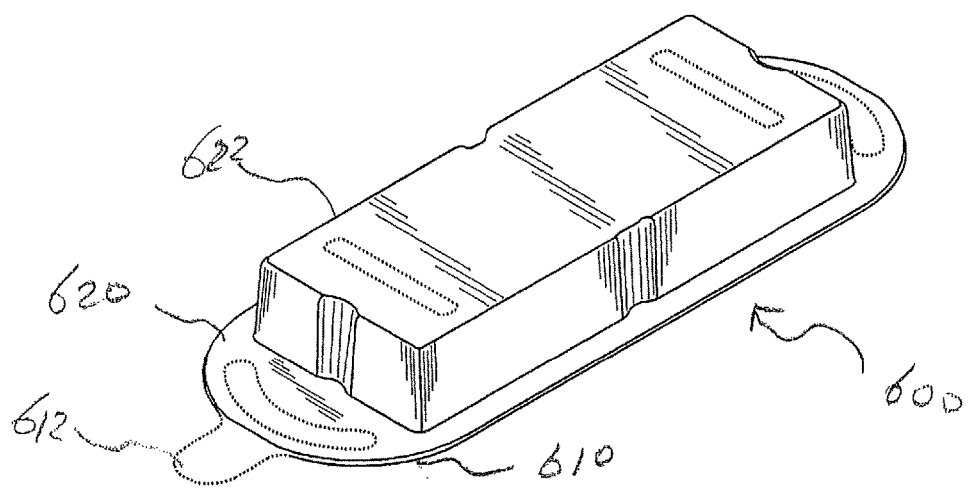

AIR PURIFIER WITH FILTER AND SCENT-RELEASING MECHANISM

CROSS-REFERENCE TO RELATED APPLICATION

This application claims the benefit of U.S. Provisional Application No. 61/834,291 filed Jun. 12, 2013, the contents of which are incorporated herein by reference.

FIELD OF THE INVENTION

The present invention generally relates to an agent or particle delivery appliance. Particularly, the present invention concerns an air purifier with an air-moving device, a filter, and an agent-delivery mechanism.

BACKGROUND OF INVENTION

The ability to easily and efficiently control indoor environments is highly desirable. A number of devices have been developed to control the temperature, humidity, odor and air quality of enclosed environments such as the rooms of a house. These mechanisms may rely upon diffusion, convection, or an assisting device such as a fan to move air in order to better control the indoor environment in a room.

Furthermore, during these same months, many people develop colds and may have sinus and chest congestion. One method for helping with the symptoms associated with congestion and colds is by dispersing medicinal vapors in the air, such as menthol or the like. The medicinal vapors help reduce cold symptoms as well as sinus and chest congestion. Medicinal vapors can be released and dispersed by scent generators, similar to air fresheners. Scents can also be released and dispersed for non-medicinal purposes, such as for providing a pleasing scent or masking an unpleasant odor. It is desirable that the scent should be released only when needed, in order to avoid waste of the scent.

Users may already have a humidifier, an air purifier, or other air moving device, to control the room environment. Although a separate device may be used to disperse the scent, having another device—in addition to the device(s) to control the room environment—may be undesirable. For instance, the number of outlets in the room may be limited. Further, the number of devices needed to control all of the desired environmental characteristics in a room can result in crowding of the room.

Thus, there is a need for an appliance that enables a user to control a scent-releasing (or other agent-releasing) mechanism in combination with an air moving device and filters.

SUMMARY OF THE INVENTION

Embodiments of the present invention provide an agent-or particle releasing mechanism for an air-moving device. The agent or particle released by the agent-releasing mechanism may include scent, as well as other volatile substances such as medicinal vapors, active ingredients such as insect repellants or sleep remedies, etc. The agent-releasing mechanism includes a chamber configured to enclose an agent cartridge such as a scent cartridge, scent pad or the like, an input port, and an output port to release the agent into a flow of air moved by the air-moving device, so that the agent is dispersed throughout the room. The chamber may include a user-controllable airflow adjustment device, which may be adjusted to control the amount of the agent released through the output port. In some embodiments, the agent cartridge can have an asymmetrical configuration, notch or the like, such that it can only be installed in a predetermined orientation.

In some embodiments of the invention, an agent-releasing appliance, such as an air purifier, includes a housing, an air-moving device disposed within the housing and configured to create a flow of air, and an agent-releasing mechanism coupled to the housing. The agent-releasing mechanism includes a chamber that is configured to accept an agent-releasing material, such as an agent-cartridge, and includes a plurality of openings. At least one of the openings is configured to input air into the chamber, while at least another one of the openings is configured to direct air from the chamber to the flow of air created by the air-moving device. In one embodiment, the chamber further includes a user-controllable airflow adjustment device for controlling the size of at least one of the plurality of openings. In one embodiment, the chamber includes a door that allows access to the chamber. The user-controllable airflow adjustment device can include, for example, a shutter or slidable panel to selectively adjust an effective surface area of one or more of the openings.

In some embodiments, the one or more openings configured to direct air from the chamber to the flow of air generated by the air-moving device is provided by one or more tubes with outlets disposed in the flow of air created by the air-moving device so as to draw air from the chamber, e.g., using the Bernoulli effect.

In some embodiments, one or more air filters can be placed upstream in relation to the one or more openings of the chamber that direct air to the flow of air created by the air moving device. The air filters can include a pre-filter including activated carbon to absorb odors or other chemicals, and a paper-based filter to remove dust or other particulate matters. In one embodiment, the pre-filter can be configured to adsorb odors or chemicals (e.g., molecules or particles of certain sizes) other than the agent released by the cartridge. In some embodiments, the pre-filter and the filter can be bonded together as a unitary structure. In some embodiments, the filter can have a frame made from a biodegradable material, such as paper, wood, etc., instead of non-biodegradable materials such as plastics.

In another aspect of the invention, a method is provided for giving an agent-releasing capability to an appliance having an air-moving device disposed within a housing, in which the air-moving device is configured to create a flow of air. The method includes the step of coupling to the housing a chamber, in which the chamber is configured to accept an agent-releasing substance and having a plurality of openings. At least one of the openings is configured to input air into the chamber and at least another one of the openings is configured to direct air from the chamber to the flow of air created by the air-moving device. The chamber also includes a user-controllable airflow adjustment device for controlling the size of at least one of the plurality of openings. In a specific embodiment, the method further includes causing the at least one of the openings to be disposed within the flow of air created by the air-moving device so as to draw air from the chamber, e.g., using the Bernoulli effect.

BRIEF DESCRIPTION OF THE DRAWINGS

The above and still further objects, features and advantages of the present invention will become apparent upon consideration of the following detailed description of embodiments thereof, especially when taken in conjunction with the accompanying drawings wherein like reference numerals in the various figures are utilized to designate like components, and wherein:

FIG. 6 is a perspective view of an agent cartridge in accordance with an embodiment of the invention.

DETAILED DESCRIPTION OF PREFERRED EMBODIMENTS

Figure 1:
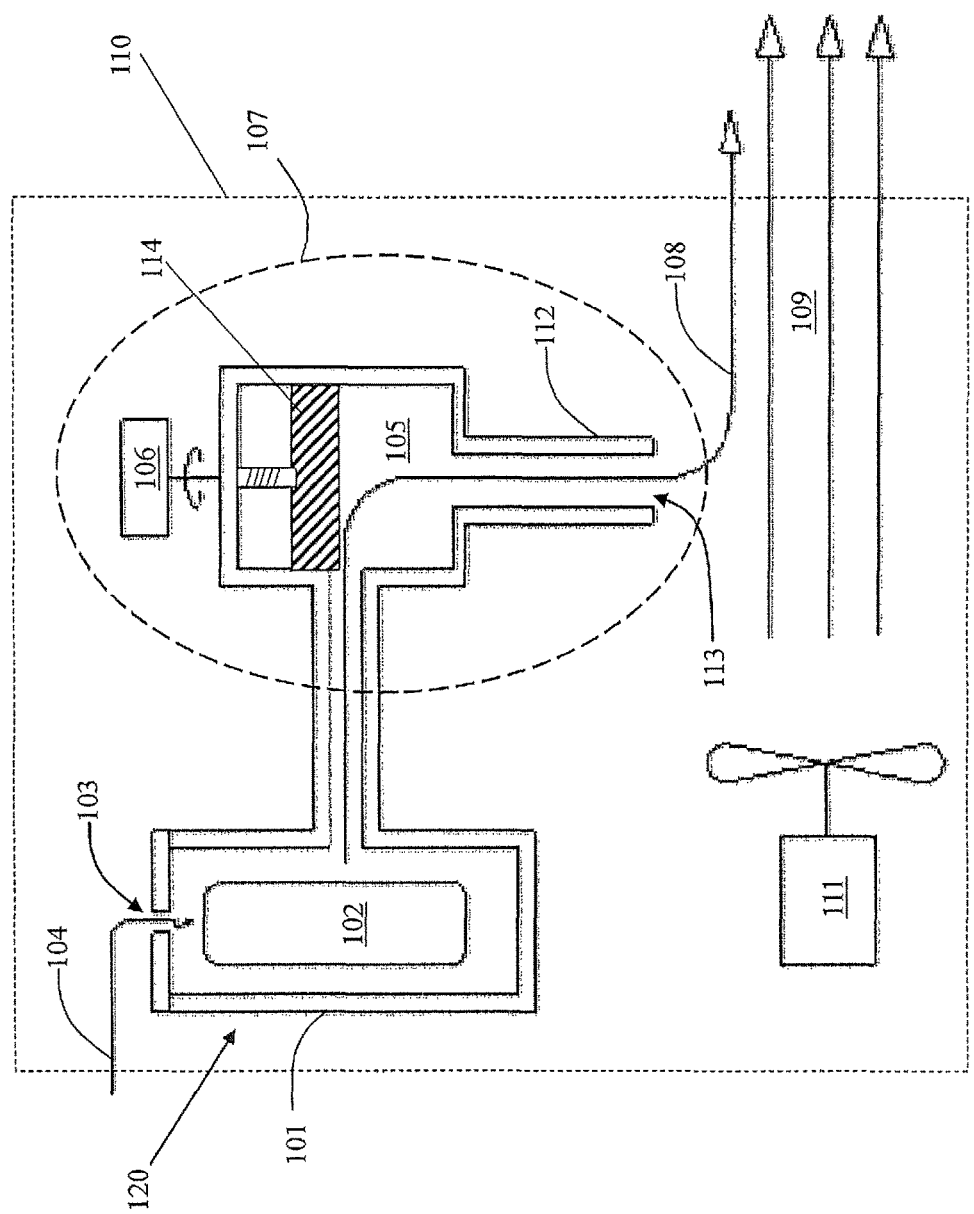
FIG. 1 is a schematic view of an air-moving device with an agent-releasing mechanism in accordance with an embodiment of the invention.

It will be readily understood that the components of the present invention, as generally described and illustrated in the figures herein, can be arranged and designed in a wide variety of different configurations in addition to the described presently preferred embodiments. Thus, the following detailed description of the embodiments of the present invention, as represented in the figures, is not intended to limit the scope of the invention, as claimed, but is merely representative of selected presently preferred embodiments of the invention. The following description is intended only by way of example, and simply illustrates certain selected presently preferred embodiments of the invention as claimed herein.

Embodiments of the present invention provide an agent-releasing mechanism that can be used with an air-moving device. The agent-releasing mechanism can be placed on or within a housing of the air-moving device such that the agent-releasing mechanism is able to controllably release the agent into the flow of air generated by the air-moving device, thus dispersing the agent within a space such as a room. The shape and configuration of the agent-releasing mechanism can be designed to match or to accommodate the housing of the air-moving device, such as by fitting within a mounting location substantially within the housing or by being attachable at a mounting location on an exterior of the housing. The agent-releasing mechanism can be fitted, attached, mounted or the like, such that a control mechanism is accessible from the exterior of the air-moving device, and such that the agent source can be replaced by a user.

The air-moving device can include a fan, but embodiments of the invention are usable with other kinds of air-moving devices such as bellows, an impeller, etc. The air-moving device is often incorporated within an environmental-control appliance such as an air purifier, a dehumidifier, a humidifier, etc.

In some embodiments, the agent to be released can include scent, as well as other chemical substances such as medicinal vapors, active ingredients such as insect repellants or sleep remedies, etc., that are desired by the user. The agent can be initially provided in the form of an agent cartridge, an agent pad, or the like. For the purposes of this disclosure, the term "agent cartridge" is used to indicate any form of carrier, cartridge, pad or otherwise that is used to hold, encapsulate or otherwise retain an agent-releasing substance; the agent cartridge itself may be made or formed, for example, from the agent such as an agent releasing substance, or an agent may be coated onto or disposed in the agent cartridge. In certain embodiments of the invention, the agent cartridge contains an agent in a volatile or evaporative form, such as a volatile solution or an evaporative solid or gel.

In some embodiments, the agent cartridge is received in a chamber. The chamber can include a door or cover that may be opened and closed by the user in order to insert or to remove the cartridge. The chamber can also have two or more relatively smaller openings, at least one being an input port that allows air to enter the chamber, and at least another opening being an output port that allows the air loaded with the agent to exit the chamber. At least one of these smaller openings can be controllably opened or closed in order to control air flowing from the input port through the chamber to the output port. For purposes of the following, the chamber can further include a tube (or tubes) or the like that directs the input and output airflows.

In some embodiments the control of the input or output port can be by way of a user-operated control mechanism (e.g., handle, knob, shutter, slidable panel or the like) that is used to adjust an intensity or amount or rate of agent delivery. The user-operated control mechanism actuates a user-controllable airflow adjustment device, such as a valve or shutter or baffle or other aperture having an adjustable opening size, to control the opening size and thereby control the volume of air passing through.

The air which passes through the adjustable opening is then introduced into a flow of air produced by the air-moving device. The flow of air draws air from the chamber out through the output port by the Bernoulli effect, which in turn draws air through the input port and into the chamber so that it may then be expelled via the output port as air loaded with the agent. A tube or the like may be used to help introduce air from the output port into the flow of air, and to introduce the air in a direction that facilitates drawing air from the tube. Adjusting the air flow through the chamber may affect the rate of evaporation of the agent. Increasing the rate of air flow through the chamber may increase the amount of agent released from the cartridge into the flow of air generated by the air-moving device.

FIG. 1 illustrates a schematic view of an embodiment of the invention. An agent-delivery appliance 100 includes an agent-releasing mechanism 120 disposed within a housing 110 together with an air-moving device 111. Agent-releasing mechanism 120 includes a chamber 101 that is mechanically coupled to housing 110, either directly, indirectly through intermediate components, or formed as part of housing 110. Chamber 101 is configured to enclose an agent cartridge 102. Chamber 101 includes an input port 103, in the form of an aperture, which allows an input stream air 104 to enter chamber 101. Chamber 101 includes an output port 113, and may also include a user-controllable airflow adjustment device 107, which is shown in FIG. 1 as further including a valve 105 that can be controlled by a user-operated knob 106. The knob 106 can be connected to a shutter or slidable panel 114 that increases or reduces the effective surface area of the output port 113 through which an output stream of air 108 can flow. In alternative embodiments (not illustrated in FIG. 1), Chamber 101 may include a user-controllable airflow adjustment device at the input port 103, or at both input port 103 and output port 113 that may be separately adjustable or co-adjustable.

Referring again to FIG. 1, output port 113 may also include a tube 112 that is used to help introduce the output stream of air 108 into a flow of air 109 generated by air-moving device 111. Tube 112 makes it possible to dispose output port 113 within the air flow 109. The flow of air 109 draws air from the Chamber 101 out through output port 113 by the Bernoulli effect. The air flow 109 is produced by existing air-moving device 111 that is part of the appliance 100. Valve 105 together with knob 106 serves as an airflow adjustment device that controls the flux of air in output stream 108, and thus the intensity of agent release from the agent-delivery appliance 100.

Separately adjustable effective surface areas of input ports 103 and output ports 113, each being adjusted by a corresponding user-controllable airflow adjustment device, may be useful, for instance, if a first port is used to set the agent-delivery appliance 100 to a predetermined intensity of agent release, and a second port is used to enable or disable agent release (e.g., by substantially fully opening or substantially fully closing the input port 103 or output port 113). Hence, one of the two user-controllable airflow adjustment devices may support a range of effective surface areas for its respective port 103, 113 that the user may select, from between fully open to fully closed and numerous intermediate states in between fully open and fully closed; the other of the two user-controllable airflow adjustment devices may support only two settings for the effective surface area of its corresponding port 103, 113, being either fully open or fully closed.

Figure 2A:
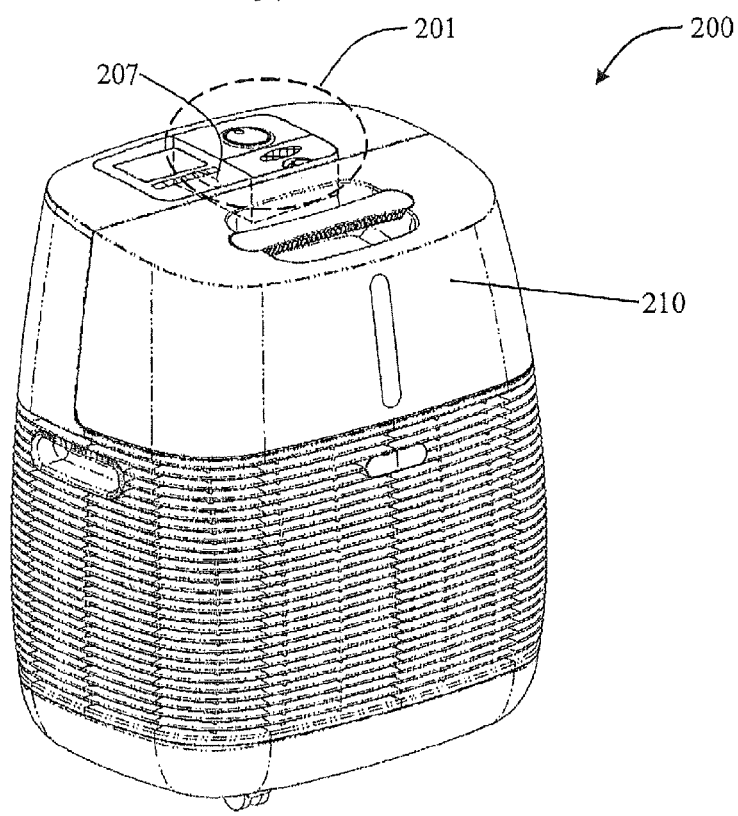
FIG. 2A is a front, left and elevated perspective view of an air-moving device with an agent-releasing mechanism in accordance with an embodiment of the invention.
Figure 2B:
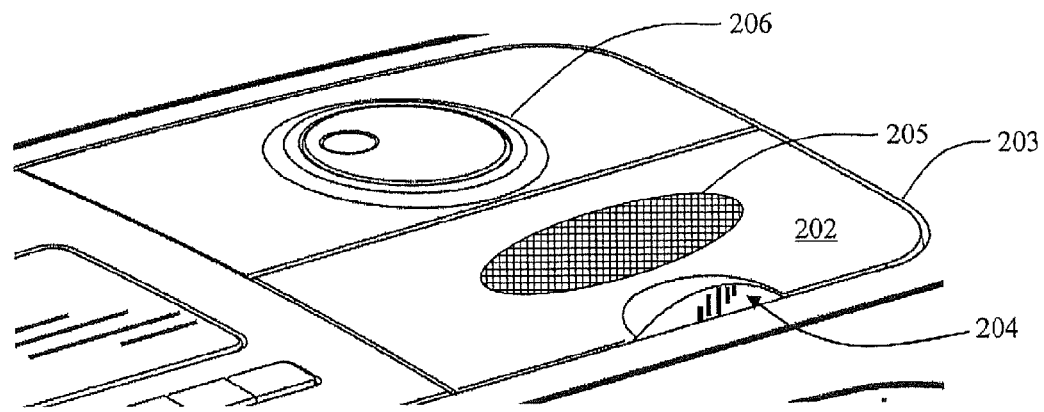
FIG. 2B is a magnified view of a portion of FIG. 2A.

FIG. 2A illustrates a perspective view of an embodiment appliance 200. Portion 201 of appliance 200 is presented in a magnified view in FIG. 2B. An openable door 202 provides access to the chamber 203, and can be closed to substantially seal off chamber 203 but for the input and output ports. Door 202 can serve as part of the exterior of housing 210 of appliance 200. Door 202 is illustrated as including a user-operable portion 204 such as a handle, raised portion or the like in order to facilitate opening and closing of door 202. Other mechanisms can be used to facilitate opening and closing of door 202, such as a spring-loaded latch, magnets, etc. An input port 205 is formed in order to provide an opening into chamber 203. Chamber 203 is disposed within the exterior surface of housing 210 and may be formed, for example, contiguously as part of housing 210 or as a separate component coupled to housing 210. Input port 205 may be formed in door 202 as illustrated, or can be formed through a sidewall of chamber 203. Input port 205 may be shaped to provide a pleasing design, such as curved openings, etc. An output port 207 of chamber 203, disposed within housing 210 and thus normally not visible from the exterior of appliance 200, is shown in dotted lines for illustration purposes herein and leads to an air flow in the interior of appliance 200 that is produced by appliance 200. A knob 206, which is operable by a user, controls the opening size of the output port 207 from chamber 203, such as by a shutter, slidable panel or like, that selectively increases or decreases the effective surface area of output port 207; the effective surface area of output port 207 is the cross-sectional area of output port 207 that a flux of air can pass through as modified by the mechanism of knob 206. Typically the effective surface area of the output port 207 is determined by a subsection or region of the output port 207 that is directly affected by the mechanism controlled by knob 206 (i.e., a shutter, sliding panel or the like). Knob 206 and its related mechanism thus serve as an airflow adjustment device, controllable by a user, to control the intensity of agent released from appliance 200.

In operation of the embodiment of the invention 200, a user can open door 202 to insert an agent cartridge. When the user wants to introduce agent into a room containing appliance 200, the user can turn on appliance 200 (if not already on), thus producing a flow of air from appliance 200. The user can then adjust knob 206 to control the effective surface area of the output port 207 until the desired amount or intensity of agent is released into the flow of air produced by appliance 200. It will be appreciated that in other embodiments knob 206 could control the effective surface area of input port 205 to control the agent releasing intensity of appliance 200. Alternatively, the appliance 200 may not include a separate control (e.g., knob 206) to adjust the amount of agent, in which case the agent is simply provided so long as the appliance 200 is turned on and is in operation.

Figure 3:
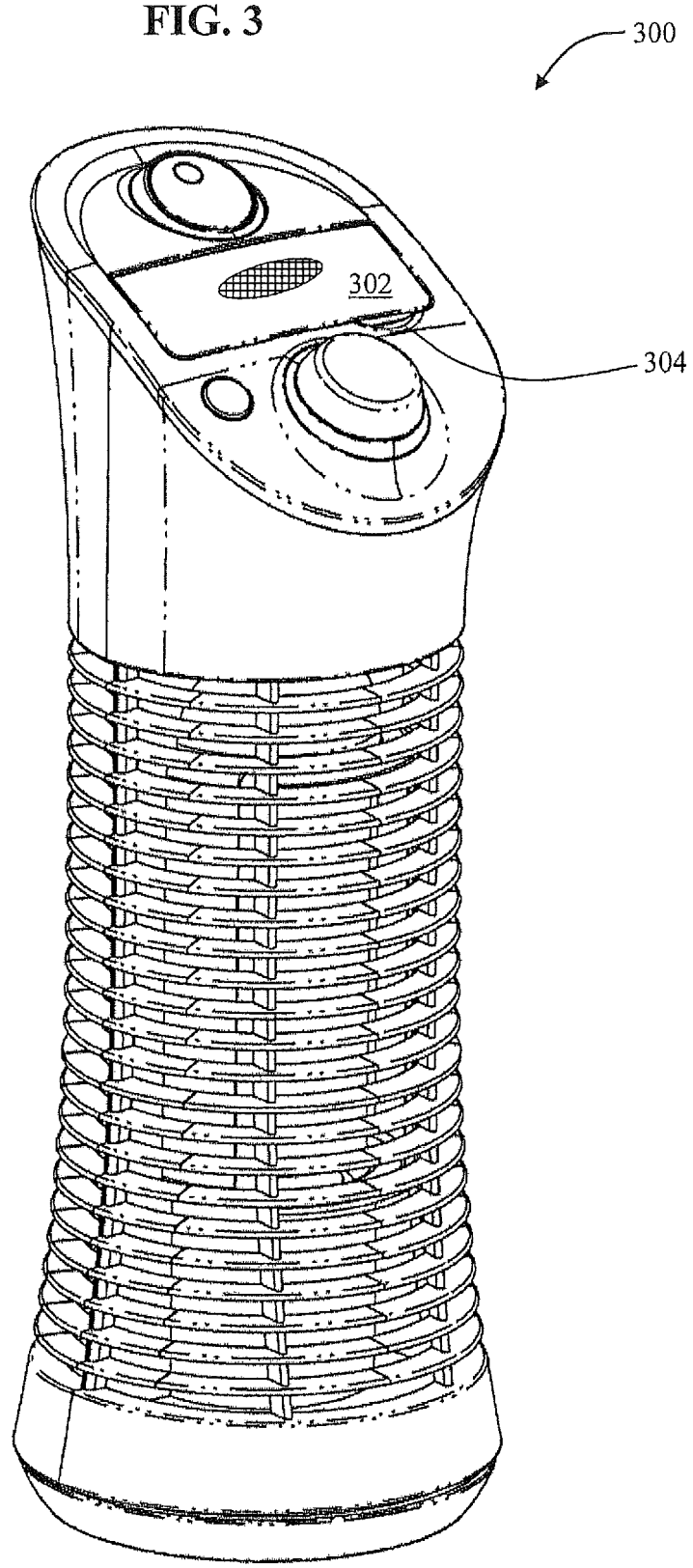
FIG. 3 is a front, left and elevated perspective view of an air-moving device with an agent-releasing mechanism in accordance with an embodiment of the invention.

FIG. 3 shows a perspective view of an appliance 300 that incorporates an agent-releasing mechanism according to an embodiment of the invention. In this embodiment 300, door 302 does not include a separate handle or the like. Rather, a portion 304 of the housing of appliance 300 is depressed, removed, or otherwise evacuated, thus exposing a side portion of door 302. The exposed side portion is a user-operable portion that can be used to open and close door 302. An agent-releasing mechanism, such as one illustrated in connection with FIG. 1 is incorporated in the appliance 300, e.g., the agent cartridge can be placed underneath the door 302.

Figure 4:
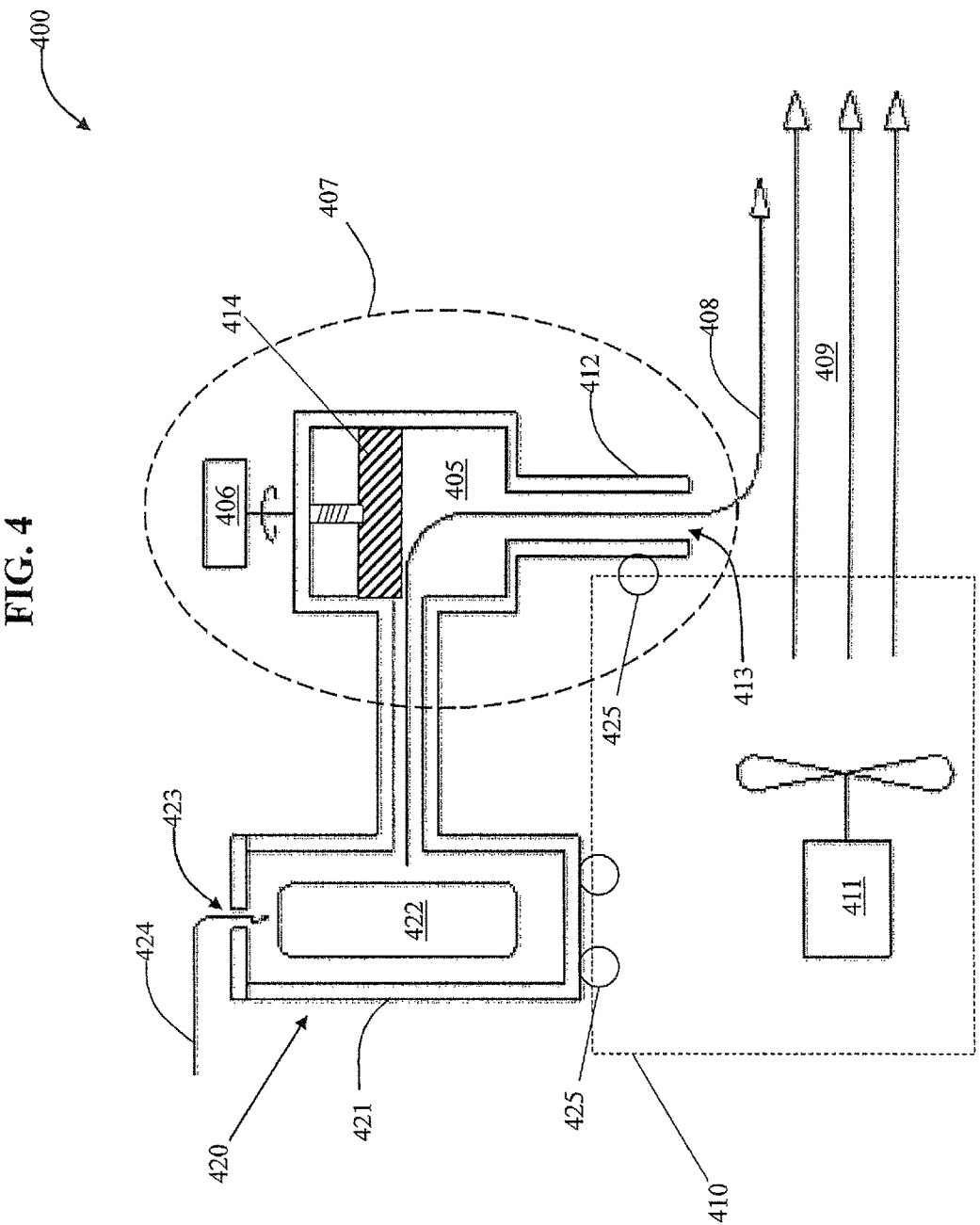
FIG. 4 is a front, left and elevated perspective view of an air-moving device with an agent-releasing mechanism in accordance with an embodiment of the invention.

FIG. 4 illustrates a schematic view of another embodiment of the invention 400. In this embodiment 400, an agent-releasing mechanism 420 is coupled to the housing 410 of the appliance 400 by way of one or more coupling mechanisms 425. Any suitable devices may be used for the coupling mechanisms 425, such as hooks, snaps, clamps, adhesives, welding points, etc. By way of example, the coupling mechanisms 425 may be configured to mechanically engage with suitable, corresponding features of the housing 410. An air-moving device 411 is disposed within the housing 410 and generates a flow of air 409 that exits from the housing 410. Agent-releasing mechanism 420 includes a chamber 421, which is externally coupled to housing 410 by way of the one or more coupling mechanism 425. Chamber 421 is configured to enclose an agent cartridge 422. Chamber 421 includes an input port 423, in the form of an aperture, which allows an input stream of air 424 to enter chamber 421. Chamber 421 includes an output port 413, and further includes a user-controllable airflow adjustment device 407, which is shown in FIG. 4 as further including a valve 405 that is controlled by a user-operated knob 406. The knob 406 is connected to a shutter or slidable panel 414 that increases or reduces the effective surface area of the output port 413 through which an output stream of air 408 can flow. Alternatively, chamber 421 may further include another user-controllable airflow adjustment device to regulate the airflow 424 into input port 423 by adjusting the effective surface area of input port 423. Alternatively, chamber 421 may include separately adjustable or co-adjustable user-controllable airflow adjustment devices.

Output port 413 is configured to be within the flow of air 409 to take advantage of the Bernoulli effect provided by the flow of air 409. For example, output port 413 may include a tube 412 that is used to help introduce the stream of air 408 exiting output port 413 into the flow of air 409 generated by air-moving device 411. Tube 412 may make it more convenient to dispose output port 413 within the air flow 409. Tube 412 may itself include a coupling mechanism 425 to couple to housing 410.

Figure 5:
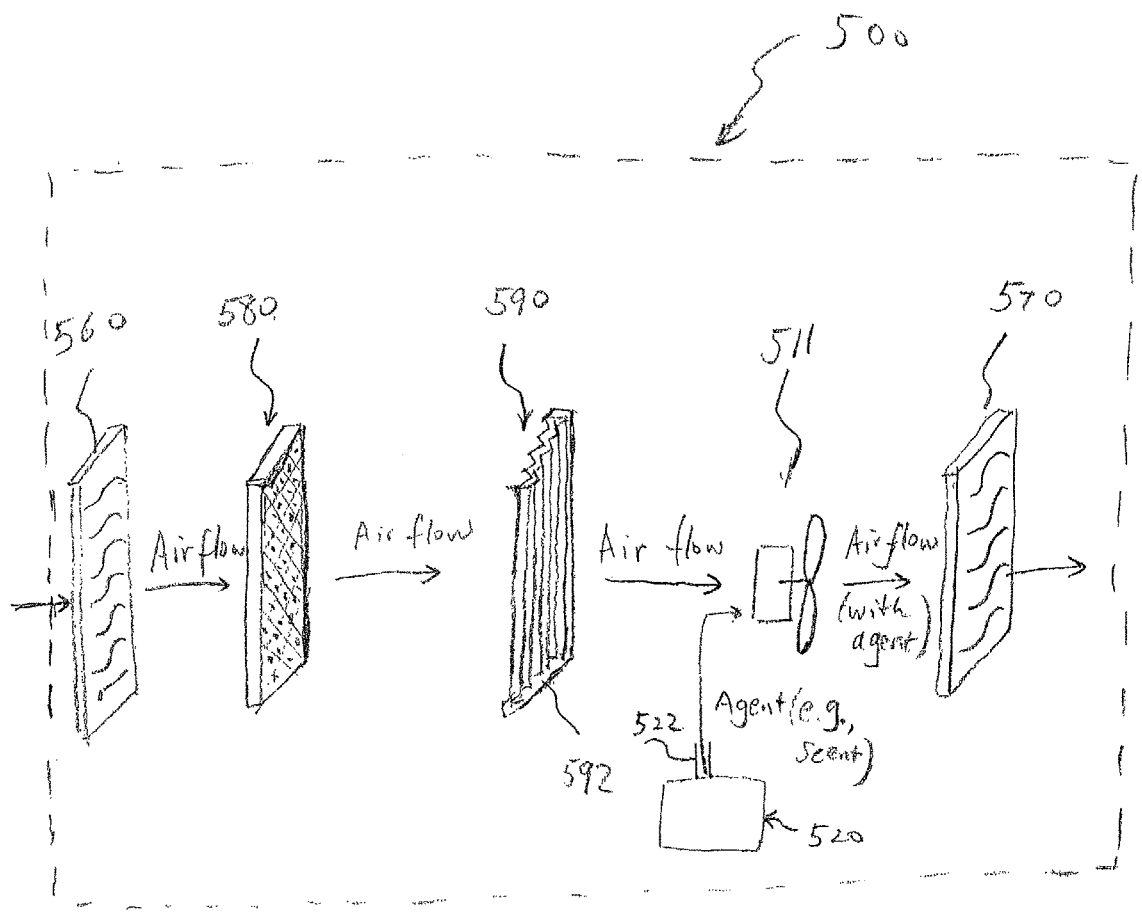
FIG. 5 is a schematic diagram of an arrangement of an agent-releasing mechanism with associated filters in accordance with an embodiment of the invention.

FIG. 5 depicts a schematic diagram of an arrangement of an agent-releasing mechanism with filters placed upstream in relation to the output port of the agent-releasing mechanism in an agent-delivery appliance according to an embodiment of the invention. As shown, the air-moving device 511 generates a flow of air that moves from upstream (left) to downstream (right). A pre-filter 580 is placed near an air inlet 560 (e.g., a first grille) of the agent-delivery appliance 500. The pre-filter can include activated carbon for adsorbing odors or other chemicals, where the activated carbon can be loaded on a foamed or porous support matrix. Placed downstream of the pre-filter 580 is a filter 590 for trapping and/or removing dust and/or other particulate matters. The filter 590 can be paper-based, or made from other cellulosic materials, and can further include synthetic fibers if desired. The filter 590 can have a frame 592 that is made from a biodegradable material, such as paper, wood, etc., instead of non-biodegradable materials such as plastics. The agent-releasing mechanism 520 can take the form as illustrated in connection with FIGS. 1 and 4 described herein, e.g., having an output port 522 positioned downstream of the pre-filter 580 and filter 590, and upstream of the air-moving device 511. Thus, the air flow after passing the air-moving device is loaded with the agent released from the agent-releasing mechanism 520, and exits from the air outlet 570 (e.g., a second grille) to the environment.

In some embodiments, the pre-filter 580 can be configured to remove odors or chemicals that are different than the agent released by the cartridge. The pre-filter can also be configured to remove molecules or particles of certain size ranges while letting other molecules or particles pass. For example, the pre-filter may be configured to remove particles greater than a certain particle size, but allow particles less than the certain particle size to pass through. The pre-filter can include adsorbents such as activated carbon and zeolites that can have their pore sizes manipulated. In this way an activated carbon layer can be created that has a preferred tendency to adsorb odors while not effectively interacting with the agent (e.g., scent) molecules through size differences. For example, mesoporous carbons could be used in the filtration layer. These carbons have the bulk of their pores in the 2-50 nm range. This range maybe effective at reducing large odor molecules but would be ineffective at removing the agent (e.g., scent) molecules that where under 2 nm. Also, both the surface of the zeolite and the activated carbon can be modified to create either hydrophobic or hydrophilic characteristics. In this manner, one could further tune the adsorbent layer to effectively reduce odor while not impacting the agent molecules. If for example the odor molecules of interest are hydrophobic in nature a hydrophilic scent could be selected that had little interaction with the hydrophobic carbon selected for odor control. In certain embodiments, the pre-filter can be configured to remove specific undesirable odors in the air or other specific chemicals. In certain embodiments, multiple pre-filters can be used, each configured to remove particular (and different) odors or other chemicals as described herein. The multiple pre-filters can be installed in the appliance in a manner that one or more of the pre-filters can be selected by the user to be operative at a given time depending on the user's need, e.g., using a control element accessible from the exterior of the appliance, such as a rotatable knob. In certain embodiments, the filter can be placed upstream of the pre-filter. In other embodiments, the pre-filter and the filter can be bonded together to form a unitary structure.

FIG. 6 is a perspective view of an agent cartridge of an agent-releasing mechanism in accordance with an embodiment of the invention. As shown, the agent cartridge 600 can have an asymmetrical configuration, include a protrusion or notch or recess (to mate with a corresponding feature in the appliance), such that it can only be installed in a predetermined orientation, for example, face up or face down. This can assist the user and insure that the cartridge is inserted in the proper orientation. The cartridge 600 can be thermoformed. For example, the cartridge can include a cover 610, a base 620 integrated with a protruding portion 622. The cover 610 can be made from paper, a metallic foil, a plastic film, and the like. The base 620 can be adhered or welded to the cover 610 to form a sealed enclosure, within which an agent source can be placed. When a user is ready to use the cartridge in an agent-delivery appliance described herein, the user can tear open and remove the cover 610 from the base, e.g., using the tab 612 which is part of the cover 610 as a grasping area, thereby exposing the agent source. Optionally, between the cover 610 and base 620 can be sandwiched another layer which is not removable with the cover 610, which layer can include a plurality of openings which are revealed upon the removal of the cover 610 from the base 620, thereby allowing the agent to be released from the cartridge. Thereafter, the user can place the cartridge 600 (with the cover removed and agent source included therein) into a chamber of an agent-releasing mechanism incorporated into an agent-delivery appliance as described herein. For example, if the chamber includes a recess dimensioned to fit the protruding portion 622, the cartridge 600 can be placed into the chamber with the protruding portion 622 fitting into the recess.

It will thus be seen that the objects set forth above, among those made apparent from the preceding description, are efficiently attained and, since certain changes may be made in the above construction(s) without departing from the spirit and scope of the invention, it is intended that all matter contained in the above description or shown in the accompanying drawing(s) shall be interpreted as illustrative and not in a limiting sense.

What is claimed is:

1. An agent-delivery appliance comprising:

a housing having at least one air inlet and at least one air outlet;

an air-moving device disposed within the housing and configured to generate a flow of air that moves from upstream to downstream such that the flow of air enters the housing through the at least one air inlet and exits the housing through the at least one air outlet;

at least one filter;

a user operable mechanism for controlling the functionality of the at least one filter; and an agent-releasing mechanism coupled to the housing;

wherein the agent-releasing mechanism comprises a chamber configured to release an agent, the chamber comprising a plurality of openings, at least one of the openings configured to provide air loaded with agent from the chamber to a first location within the flow of air generated by the air-moving device; and wherein the at least one filter is disposed upstream from the first location within the flow of air.

2. The agent-delivery appliance of claim 1 wherein the at least one filter is configured to:

remove a plurality of particles having one or more predetermined particle sizes that are larger than a molecular size of the agent, or remove a plurality of particles having a predetermined hydrophobicity/hydrophilicity condition that is different from a hydrophobicity/hydrophilicity condition of the agent, so that the at least one filter absorbs odors while not effectively interacting with the agent.

3. The agent-delivery appliance of claim 1 wherein the chamber further comprises:
a first user-controllable airflow adjustment device for controlling a size of at least one of the plurality of openings.

4. The agent-delivery appliance of claim 3 wherein:
the chamber further comprises a second user-controllable airflow adjustment device for controlling a size of at least one of the plurality of openings,
the first user-controllable airflow adjustment device providing a user-selectable range of effective surface areas, and
the second user-controllable airflow adjustment device providing a substantially fully open position and a substantially fully closed position.

5. The agent-delivery appliance of claim 1 wherein the agent-releasing mechanism further comprises a component for providing access to the chamber.

6. The agent-delivery appliance of claim 1 wherein the chamber is further configured to accept an agent cartridge.

7. The agent-delivery appliance of claim 6 wherein the agent cartridge comprises a mechanism for controlling orientation of the agent cartridge to allow installation in the chamber.

8. The agent-delivery appliance of claim 6 wherein the agent cartridge is asymmetrically shaped.

9. The agent-delivery appliance of claim 1 wherein the at least one filter comprises a pre-filter.

10. The agent-delivery appliance of claim 9 wherein the pre-filter comprises adsorbents.

11. The agent-delivery appliance of claim 1 wherein the at least one filter comprises a filter configured to remove particulate matter.

12. The agent-delivery appliance of claim 11 wherein the at least one filter comprises cellulosic materials.

13. The agent-delivery appliance of claim 11 wherein the at least one filter comprises synthetic fibers.

14. The agent-delivery appliance of claim 1 wherein the at least one filter comprises a combination of a pre-filter and a filter configured to remove particulate matter, which are coupled together to form a unitary structure.

15. The agent-delivery appliance of claim 1 wherein the at least one filter is disposed near the at least one air inlet.

16. The agent-delivery appliance of claim 1 wherein the at least one of the openings configured to provide air loaded with agent from the chamber to a first location within the flow of air generated by the air-moving device comprises a tube having an outlet disposed within the flow of air generated by the air-moving device.

17. The agent-delivery appliance of claim 1, wherein the at least one filter comprises:
a first filter comprising a pre-filter including activated carbon; and
a second filter disposed downstream from the first filter, the second filter comprising a paper filter being configured to remove particulate matter and being disposed upstream from the first location within the flow of air.

18. The agent-delivery appliance of claim 17 wherein the first filter is disposed on the at least one air inlet.

19. The agent-delivery appliance of claim 1 wherein the agent-releasing mechanism is disposed within the housing.

20. An agent-delivery appliance comprising:
a housing having at least one air inlet and at least one air outlet;
an air-moving device disposed within the housing and configured to generate a flow of air that moves from upstream to downstream such that the flow of air enters the housing through the at least one air inlet and exits the housing through the at least one air outlet;
at least one filter;
an agent-releasing mechanism coupled to the housing, wherein the agent-releasing mechanism comprises a chamber configured to release an agent, the chamber comprising a plurality of openings, wherein at least one opening of the plurality of openings is configured to provide air loaded with agent from the chamber to a first location within the flow of air generated by the air-moving device; and
a first user-controllable airflow adjustment device for controlling an effective surface area of the at least one opening of the plurality of openings;
wherein the at least one filter is disposed upstream from the first location within the flow of air; and
wherein the at least one opening of the plurality of openings that is configured to provide the air loaded with the agent from the chamber to the first location within the flow of the air comprises a tube having an outlet disposed proximate the flow of air to draw air from the chamber using the Bernoulli effect.

21. The agent-delivery appliance of claim 20 wherein the at least one filter comprises a pre-filter.

22. The agent-delivery appliance of claim 20 wherein the at least one filter comprises a filter configured to remove particulate matter.

* * * * *